(12) United States Patent
Tracy et al.

(10) Patent No.: US 6,455,074 B1
(45) Date of Patent: *Sep. 24, 2002

(54) METHODS FOR FABRICATING POLYMER-BASEDb CONTROLLED RELEASE DEVICES

(75) Inventors: Mark A. Tracy, Arlington, MA (US); John D. Herberger, Moore Park; Paul A. Burke, Oxnard, both of CA (US); Paul F. Herbert, Wayland, MA (US)

(73) Assignee: Alkermes Controlled Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/375,090

(22) Filed: Aug. 16, 1999

Related U.S. Application Data

(62) Division of application No. 08/935,452, filed on Sep. 24, 1997, now Pat. No. 5,989,463.

(51) Int. Cl.⁷ .............................. A61F 2/16; A61K 9/48; B32B 27/02; B32B 5/16; B01J 13/02
(52) U.S. Cl. ..................... 424/501; 424/502; 424/426; 428/402.21; 264/4.1; 264/4.3; 264/4.33
(58) Field of Search ................... 424/501, 502, 424/426; 428/402.21; 264/4.1, 4.3, 4.33

(56) References Cited

U.S. PATENT DOCUMENTS

| | | | |
|---|---|---|---|
| 5,192,741 A | 3/1993 | Orsolini et al. ................. 514/4 |
| 5,307,640 A | 5/1994 | Fawzy et al. ................. 62/52.1 |
| 5,401,502 A | 3/1995 | Wunderlich et al. ..... 424/195.1 |
| 5,475,984 A | 12/1995 | Fermani et al. ................. 62/64 |
| 5,478,564 A | 12/1995 | Wantier et al. ............. 424/426 |
| 5,540,937 A | 7/1996 | Billot et al. ................. 424/489 |
| 5,556,642 A | 9/1996 | Kobayashi et al. ......... 424/502 |
| 5,585,460 A | 12/1996 | Yamada et al. ............. 528/491 |
| 5,594,091 A | 1/1997 | Igari et al. ................... 528/271 |
| 5,609,886 A | 3/1997 | Wantier et al. ............. 424/497 |
| 5,650,173 A | 7/1997 | Ramstack et al. .......... 424/489 |
| 5,654,010 A | 8/1997 | Johnson et al. ............. 424/502 |
| 5,656,297 A | 8/1997 | Bernstein et al. ........... 424/484 |
| 5,667,808 A | 9/1997 | Johnson et al. ............. 424/501 |
| 5,674,534 A | 10/1997 | Zale et al. .................. 424/501 |
| 5,711,968 A | 1/1998 | Tracy et al. ................. 424/487 |
| 5,716,644 A | 2/1998 | Zale et al. .................. 424/497 |
| 5,989,463 A | * 11/1999 | Tracy et al. ................. 264/4.1 |

FOREIGN PATENT DOCUMENTS

| | | |
|---|---|---|
| EP | 0 190 833 | 8/1986 |
| EP | 0 556 917 | 8/1993 |
| EP | 0 586 838 | 3/1994 |
| WO | WO 95/29664 | 11/1995 |
| WO | WO 96/12478 | 5/1996 |
| WO | WO 96/19201 | 6/1996 |
| WO | WO 97/07788 | 3/1997 |
| WO | WO 97/42940 | 11/1997 |

* cited by examiner

*Primary Examiner*—Carlos Azpuru
(74) *Attorney, Agent, or Firm*—Hamilton, Brook, Smith and Reynolds, P.C.

(57) ABSTRACT

The present invention relates to a polymer-based sustained release device, and methods of forming and using the device for the sustained release of an active agent. The improved method of the invention for forming a polymer-based sustained release device comprises forming a polymer/active agent solution by mixing a polymer, a continuous phase, and an active agent. The continuous phase can comprise one or more polymer solvents, a polymer solvent/polymer non-solvent mixture, or a polymer solvent/active agent non-solvent mixture. When the continuous phase comprises a polymer solvent/active agent non-solvent, the active agent can also be present as a microparticulate rather than in solution. The continuous phase is then removed from the polymer/active agent solution, thereby forming a solid polymer/active agent matrix.

52 Claims, 2 Drawing Sheets

METHODS FOR FABRICATING POLYMER-BASED CONTROLLED RELEASE DEVICES

RELATED APPLICATIONS

This application is a Divisional of U.S. application Ser. No. 08/935,452 filed Sep. 24, 1997, now U.S. Pat No. 5,989,463, the entire teachings of which are incorporated herein by reference.

BACKGROUND OF THE INVENTION

Many illnesses or conditions require administration of a constant or sustained level of a medicament or biologically active agent to provide the most effective prophylactic or therapeutic effect. This may be accomplished through a multiple dosing regimen or by employing a system that releases the medicament in a sustained fashion.

Systems for delivering sustained levels of medication have employed biodegradable materials, such as polymers, encapsulating the medicament. The use of biodegradable polymers, for example, in the form of microparticles or microcarriers, provides a sustained release of medicaments, by utilizing the inherent biodegradability of the polymer to control the release of the medicament thereby providing a more consistent, sustained level of medication and improved patient compliance.

Certain methods of fabricating polymer-based sustained release devices comprise the steps of dissolving a polymer in a solvent, adding to the polymer solution the active agent to be incorporated and removing the solvent from the mixture thereby forming a matrix of the polymer with the active agent distributed throughout the matrix.

Many of these methods of fabricating polymer-based sustained release devices employ a solvent or mixture of solvents, which solubilizes the polymer, but are not capable of solubilizing the active agent to be incorporated. Hence, these methods have disadvantages, for example, in the lack of suitable solvents which are capable of dissolving both active agent and polymer and which are non-toxic, biocompatible and can be readily removed from the final product; in solubilizing of the active agent in an active form; and in optimizing encapsulation efficiency of the active agent to achieve a device with the desired release characteristics.

Therefore, a need exists for improved methods for fabricating a polymer-based sustained release device, particularly devices having a high load of active agent.

SUMMARY OF THE INVENTION

The present invention is based upon the discovery that an improved polymer-based sustained release device can be achieved when a continuous phase which is capable of solubilizing both the polymer and the active agent is employed in the method for fabricating the device. Unexpectedly, an advantage of the sustained release devices obtained thereby is that they can have a very high load of active agent. For example, the device can achieve a relative weight of active agent in excess of the total polymer weight (e.g., present at about 50% by weight or more of the total weight of the device) with improved encapsulation efficiency and improved sustained release characteristics.

An additional advantage of the invention is that it allows for the preparation of small microparticles which contain encapsulated drug and exhibit improved delivery characteristics. A further advantage is the ability to use solubility properties of the active agent to affect particle size of the active agent, further enabling improved delivery characteristics. Additionally, the process for preparing microparticles may be improved by permitting the ability to filter sterilize process components or facilitate atomization of the polymer/active agent solution or dispersion.

The present invention thus relates to a polymer-based sustained release device, and methods of forming and using said device for the sustained release of an active agent. The improved method of the invention, for forming the polymer-based sustained release device, utilizes a continuous phase which comprises, for example, one or more polymer solvents, a polymer solvent/polymer non-solvent mixture or a polymer solvent/active agent non-solvent mixture, to dissolve the polymer and also solubilize the active agent in the polymer solution. Also embraced by the invention described herein is a process wherein the continuous phase comprises a polymer solvent/active agent non-solvent mixture and the active agent is present as a microparticulate. For purposes of the invention, the term "microparticulate" describes the situation where the active agent is dispersed in the continuous phase at a concentration of the active agent approaching solubilization of the active agent or where the active agent is present as a combination of both dispersed particulate and solubilized active agent. Typically, the microparticulate is formed by mixing an active agent non-solvent with a solution containing the active agent which thereby leads to partial or complete precipitation of the active agent (also referred to as the "Microparticulate Method").

In one embodiment, the method comprises (a) forming a polymer/active agent solution by mixing a polymer, a continuous phase comprising one or more polymer solvents and an active agent wherein the polymer and active agent are present in relative concentrations such that the final product contains about 50% by weight or more of active agent; and (b) removing the continuous phase of step (a) thereby forming a solid polymer/active agent matrix.

The method can further comprise the step of forming droplets of the polymer/active agent solution prior to removal of the continuous phase. Further, the method can comprise freezing the droplets prior to removal of the continuous phase. According to the method of the invention the droplets can be microdroplets. In a specific embodiment wherein droplets are formed and then frozen, the continuous phase can be removed by an extraction process. Alternatively, the continuous phase can be removed by an evaporation process or a combination of an evaporation and extraction process.

When the continuous phase comprises one or more polymer solvents any combination of polymer solvents which is miscible and allows both the polymer and active agent to be dissolved, is suitable for use in the invention. Dimethylsulfoxide (also referred to as DMSO) is preferred because it is a good solvent for many polymers and active agents, including water-soluble agents such as peptides, antigens, and small molecule drugs. Other suitable solvents. in particular for PLGA polymers include, DMSO, ethyl acetate, methyl acetate, methylene chloride, chloroform, hexafluoroisopropanol, acetone, and combinations thereof. Preferably, the polymer solvent is pharmaceutically acceptable.

In another embodiment, the method for forming a polymer-based sustained release device comprises the steps of: (a) forming a polymer/active agent solution by mixing a polymer, an effective amount of an active agent and a continuous phase comprising a polymer solvent/polymer non-solvent mixture wherein the amount of polymer non-solvent is dictated by achieving solubilization of the active agent without causing substantial precipitation of the polymer; and (b) removing the continuous phase of step (a) from the polymer/active agent solution, thereby forming a solid polymer/active agent matrix. In a further embodiment, the active agent is present at a concentration such that the final product or device contains about 50% by weight or more of active agent.

The method can further comprise the step of forming droplets of the polymer/active agent solution prior to removal of the continuous phase. Further, the method can comprise freezing the droplets prior to removal of the continuous phase. According to the method of the invention the droplets can be microdroplets. In a specific embodiment wherein droplets are formed and then frozen, the continuous phase can be removed by an extraction process. Alternatively, the continuous phase can be removed by evaporation process or a combination of an evaporation and extraction process.

The polymer non-solvent can be selected such that it is miscible with the polymer solvent, does not cause substantial precipitation of the polymer and is not deleterious to the active agent. Preferably, the polymer solvent and the polymer non-solvent are pharmaceutically acceptable.

Suitable polymer non-solvents include, for example, ethanol, methanol, water, acetonitrile (MeCN), dimethylformamide (DMF), ethyl ether, alkanes such as pentane, isopentane, hexane, heptane and oils, such as mineral oils, fish oils, silicone oils, vegetable oils, or combinations thereof. Vegetable oils, such as olive oil, sesame oil, soybean oil, safflower oil, peanut oil, cottonseed oil, coconut oil, linseed oil, corn oil, castor oil, palm oil, or combinations thereof, are preferred for use in the invention. In particular embodiments, the polymer solvent is DMSO and the non-solvent is ethanol or water.

In another embodiment, the method for forming a polymer-based sustained release device comprises the steps of: (a) forming a polymer/active agent mixture by mixing a polymer, an effective amount of an active agent and a continuous phase comprising a polymer solvent/active agent non-solvent mixture wherein the amount of active agent non-solvent is dictated by achieving solubilization of the active agent, or alternatively achieving the active agent as a microparticulate in the continuous phase containing the polymer; and (b) removing the continuous phase of step (a) thereby forming a solid polymer/active agent matrix. In a further embodiment, the active agent is present at a concentration such that the final product or device contains about 50% by weight or more of active agent.

The method can further comprise the steps of forming droplets of the polymer/active agent solution prior to removal of the continuous phase. Further, the method can comprise freezing the droplets prior to removal of the continuous phase. According to the method of the invention the droplets can be microdroplets. In a specific embodiment wherein droplets are formed and then frozen, the continuous phase can be removed by an extraction process. Alternatively, the continuous phase can be removed by evaporation process or a combination of an evaporation and extraction process.

The active agent non-solvent can be selected such that it is miscible with the polymer solvent, does not substantially precipitate the polymer, and is not deleterious to the active agent. Suitable active agent non-solvents are dependent upon the properties of the active agent and for peptides can include, for example, acetone, ethanol and methylene chloride.

In another aspect, the invention relates to a polymer-based sustained release device prepared according to the method of the invention. The device comprises a polymeric matrix and an active agent dispersed within the matrix. The device formed by the method of the invention exhibits a unique microstructure, the porosity of which varies as a function of load, polymer concentration and the type of continuous phase employed.

The method of using the polymer-based sustained release device of the present invention comprises providing a sustained delivery of active agent, in a subject, over a therapeutically useful period of time, by administering to the subject a dose of said polymer-based sustained release device. The invention also provides methods for preparing microparticles of varying size and/or morphology for use in specific applications, for example, applications such as chemoembolization, vaccine delivery or cellular uptake where the size of the microparticles directly impacts performance.

Figure 1:
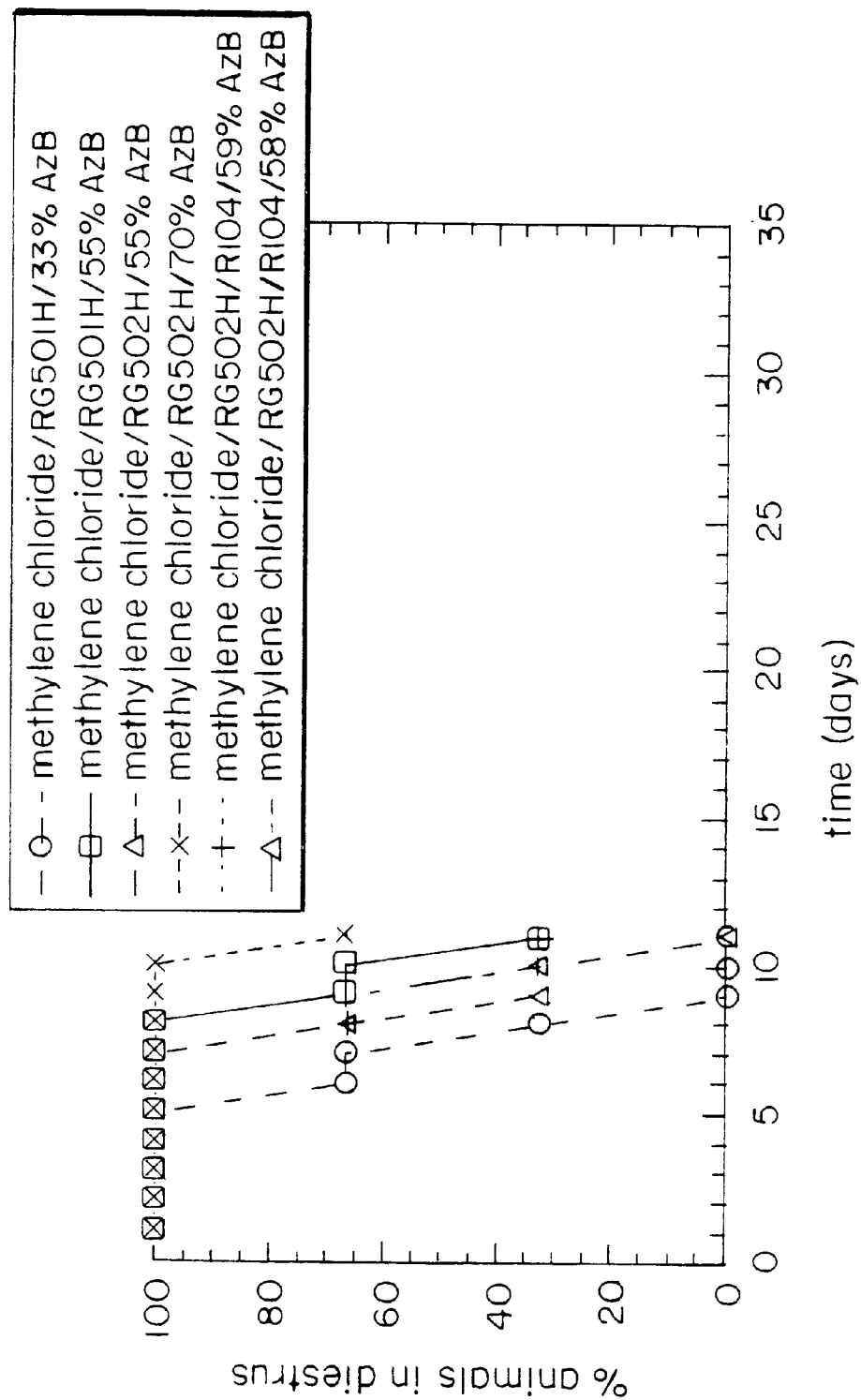
FIG. 1 is a plot of the percent of animals per treatment group in diestrus for groups of rats treated with microparticles prepared using the Particulate Method, as described herein, and having the indicated load of azaline B versus time.

The foregoing and other objects, features and advantages of the invention will be apparent from the following more particular description of preferred embodiments of the invention.

DETAILED DESCRIPTION OF THE INVENTION

The features and other details of the invention will now be more particularly described and pointed out here as well as in the claims. It will be understood that the particular embodiments of the invention are shown by way of illustration and not as limitations of the invention. The principle features of this invention can be employed in various embodiments without departing from the scope of the invention.

A solution, as defined herein, is a mixture of one or more substances (referred to as the solute, for example, the polymer and the active agent) dissolved in one or more other substances (referred to as the solvent or solvents, for example, DMSO or a combination of DMSO and methylene chloride). For purposes of this invention, the "continuous phase" refers to the major component of a solution, such as a polymer solvent or a mixture thereof, and a mixture of a polymer solvent and a non-solvent.

The term "non-solvent," as used herein, refers to a material, which does not substantially dissolve a second or reference material. For purposes of this invention, the non-solvent can be a non-solvent for the active agent or the polymer.

The term "microdroplet," as used herein, refers to a droplet of any morphology which has a dimension less than or equal to about 1000 μm.

The active agent, azaline B, used in many of the examples described herein is an LHRH peptide analog, the structure of which is described in, for example, Campen et al., *Biochemical Pharmacology* 40: 1313–1321, 1995, and which can be depicted as follows:

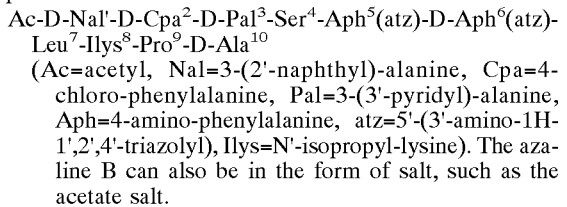

Ac-D-Nal'-D-Cpa²-D-Pal³-Ser⁴-Aph⁵(atz)-D-Aph⁶(atz)-Leu⁷-Ilys⁸-Pro⁹-D-Ala¹⁰

(Ac=acetyl, Nal=3-(2'-naphthyl)-alanine, Cpa=4-chloro-phenylalanine, Pal=3-(3'-pyridyl)-alanine, Aph=4-amino-phenylalanine, atz=5'-(3'-amino-1H-1',2',4'-triazolyl), Ilys=N'-isopropyl-lysine). The azaline B can also be in the form of salt, such as the acetate salt.

In one aspect, the invention provides an improved method for preparing a polymer-based sustained release device comprising the use of a continuous phase which comprises one or more polymer solvents, a mixture of one or more polymer solvents with one more polymer non-solvents or a mixture of one or more polymer solvents with one or more active agent non-solvents, to dissolve the polymer and also solubilize the active agent in the polymer solution. When the continuous phase comprises a polymer solvent/active agent non-solvent, the situation where the active agent is present as a microparticulate is also embraced within the invention described herein.

In one embodiment, the method comprises (a) forming a polymer/active agent solution by mixing a polymer, a continuous phase comprising one or more polymer solvents and an active agent wherein polymer and active agent are present in relative concentrations such that the final product or device contains about 50% by weight or more of active agent; and (b) removing the continuous phase of step (a) thereby forming a solid polymer/active agent matrix.

The method can further comprise the step of forming droplets of the polymer/active agent solution prior to removal of the continuous phase. Further the method can comprise freezing the droplets prior to removal of the continuous phase. According to the method of the invention the droplets can be microdroplets. In a specific embodiment wherein droplets are formed and then frozen, the continuous phase can be removed by an extraction process. Alternatively, the continuous phase can be removed by evaporation process or a combination of an extraction and evaporation process.

When the continuous phase comprises one or more polymer solvents any combination of polymer solvents which is miscible and allows both the polymer and active agent to be dissolved, is suitable for use in the invention. Dimethylsulfoxide (also referred to as DMSO) is a preferred solvent because it is a good solvent for many polymers and active agents, including peptides, antigens and small molecule drugs. Other suitable solvents, in particular for PLGA polymers, include, for example, DMSO, ethyl acetate, methyl acetate, methylene chloride, chloroform, hexafluoroisopropanol and acetone. Preferably, the polymer solvent is pharmaceutically acceptable.

The method wherein one or more polymer solvents can be used as the continuous phase can be referred to herein as the "Polymer Solvent Method" indicating that the major component of the continuous phase of the method comprises, or consists essentially of, one or more polymer solvents. If more than one polymer solvent is employed, it is understood that one of the polymer solvents can also be a non-solvent for the active agent provided that the active agent remains soluble in the continuous phase.

In another embodiment, the method for forming a polymer-based sustained release device comprises the steps of: (a) forming a polymer/active agent solution by mixing a polymer, an effective amount of an active agent and a continuous phase comprising a polymer solvent/polymer non-solvent mixture wherein the amount of non-solvent is dictated by achieving solubilization of the active agent without causing substantial precipitation of the polymer; and (b) removing the continuous phase of step (a) from the polymer/active agent solution, thereby forming a solid polymer/active agent matrix. In a further embodiment, the active agent is present at a concentration such that the final product or device contains about 50% by weight or more active agent.

The method can further comprise the step of forming droplets of the polymer/active agent solution prior to removal of the continuous phase. Further, the method can comprise freezing the droplets prior to removal of the continuous phase. According to the method of the invention the droplets can be microdroplets. In a specific embodiment wherein droplets are formed and then frozen, the continuous phase can be removed by an extraction process. Alternatively, the continuous phase can be removed by evaporation process or a combination of an extraction and evaporation process.

The method wherein the continuous phase comprises a polymer solvent/polymer non-solvent mixture, can be referred to as the "Polymer Solvent/Polymer Non-Solvent Method." When the major component of the continuous phase comprises, or consists essentially of, a polymer solvent/polymer non-solvent mixture a combination or one or more polymer solvents with one or more polymer non-solvents can be employed. The amount and type of polymer non-solvent can be selected such that it is completely or substantially miscible with the polymer solvent, does not cause substantial precipitation of the polymer, and is not deleterious to the active agent. Preferably, the polymer solvent and the polymer non-solvent are pharmaceutically acceptable. It is understood that one or both solvents in the continuous phase can serve to solubilize the active agent.

Polymer non-solvents suitable for use in the invention include, for example, ethanol, methanol, water, acetonitrile (MeCN), dimethylformamide (DMF), ethyl ether, alkanes, such as pentane, isopentane, hexane or heptane, and oils, such as mineral oils, fish oils, silicone oil, vegetable oils, or any combination thereof. Vegetable oils, such as olive oil, sesame oil, soybean oil, safflower oil, peanut oil, cottonseed oil, coconut oil, linseed oil, corn oil, castor oil, palm oil, or combinations thereof, are preferred for use in the invention. In particular embodiments, the polymer solvent is DMSO and the non-solvent is ethanol or water.

In another embodiment, the method for forming a polymer-based sustained release device comprises the steps of: (a) forming a polymer/active agent mixture by mixing a polymer, an effective amount of an active agent and a continuous phase comprising a polymer solvent/active agent non-solvent mixture wherein the amount of active agent non-solvent is dictated by achieving solubilization of the active agent, or alternatively achieving the active agent as a microparticulate, in the continuous phase containing the polymer; and (b) removing the continuous phase of step (a) thereby forming a solid polymer/active agent matrix. In a further embodiment, the active agent is present at a concentration such that the final product or device contains about 50% by weight or more of active agent.

The method can further comprise the step of forming droplets of the polymer/active agent solution prior to removal of the continuous phase. Further, the method can comprise freezing the droplets prior to removal of the continuous phase. According to the method of the invention the droplets can be microdroplets. In a specific embodiment wherein the droplets are formed and then frozen, the continuous phase can be removed by an extraction process. Alternatively, the continuous phase can be removed by an evaporation process or a combination of an extraction and evaporation process.

The amount and type of active agent non-solvent can be selected such that it is miscible with the polymer solvent, does not substantially precipitate the polymer, and is not deleterious to the active agent. Suitable active agent non-solvents are dependent upon the properties of the active agent and for peptides can include, for example, acetone, ethanol and methylene chloride.

Other excipients can be present in the polymer/active agent solution, as described below. These excipients need not be soluble in the continuous phase, although, this is preferred.

The active agent of the invention can be added either as a solid (such as in a fine powder) or neat liquid, or as a solution of the active agent in the polymer solvent or polymer non-solvent.

It can be desirable to add a polymer non-solvent which is a solvent for the active agent to the polymer solvent when forming the polymer/active agent solution if, for example, the polymer solvent does not solubilize the active agent to the desired degree. The polymer non-solvent should be miscible with the polymer solvent, aid in solubilizing the active agent, not cause substantial precipitation of the polymer and not be deleterious to the active agent. An example of such an embodiment is in the formation of a solution of PLGA and tRNA. DMSO is a good solvent for PLGA but poorly solubilizes tRNA. The inclusion of, for example, water (a good solvent for tRNA, miscible with DMSO and a non-solvent for the polymer) results in an optically transparent solution comprising PLGA, tRNA, DMSO and water. Therefore, the continuous phase, in this embodiment, comprises a polymer solvent/non-solvent mixture, wherein the non-solvent is a non-solvent for the polymer. The amount of polymer non-solvent included is at least that amount necessary to achieve the desired level of solubilization of the active agent but not to exceed that amount which causes substantial precipitation of the polymer.

It can also be desirable to add a polymer non-solvent, which is a non-solvent for the active agent, to the polymer solvent when forming the polymer/active agent solution, if, for example, the polymer solvent solubilizes the active agent to a greater degree than desired. For example, in such an embodiment, the active agent may "leach" out of the microdroplet with the polymer solvent during the extraction step of the process. The addition of the active agent non-solvent can minimize this effect. The polymer non-solvent should be miscible with the polymer solvent and assist in decreasing the solubility of the active agent in the resulting polymer solvent/non-solvent mixture.

In summary, one aspect of the invention relates to maximizing polymer and active agent solubility properties in the continuous phase by selecting the appropriate solvent or combination of solvents. Thus, the addition or selection of appropriate solvents, co-solvents, or non-solvents results in the improved microparticles described herein.

The continuous phase can be formed prior to, following or simultaneous with the addition of the polymer to the polymer solvent. The active agent can be mixed with the polymer solution either as a solid, a neat liquid or in solution. When the active agent is added in solution the solvent of the active agent solution can be a polymer non-solvent, polymer solvent or combinations thereof. Further, when the active agent is added as a solid or neat liquid, which is not soluble in the polymer solution, an additional polymer solvent, polymer non-solvent or combinations thereof can be added which solubilizes the active agent.

For example, poly(lactide-co-glycolide) was dissolved in DMSO and the active agent, ovalbumin, was predissolved in a minimum amount of water (a polymer non-solvent) and added to the polymer solution to form the polymer/active agent solution, thereby providing a continuous phase comprising a polymer solvent/polymer non-solvent mixture.

In another example, poly(lactide-co-glycolide) was dissolved in DMSO and the active agent, tRNA, was predissolved in a minimum amount of water and added to the polymer solution to form the polymer/active agent solution.

In yet another embodiment, the active agent can be added as a solid, to a mixture of polymer solvent/polymer non-solvent having the polymer dissolved therein. The solid is soluble in the mixture. In a specific embodiment, the continuous phase comprising the polymer solvent/polymer non-solvent mixture, is DMSO and ethanol. In a more specific embodiment, the polymer of the polymer solution includes poly(lactide-co-glycolide) dissolved in a DMSO/ethanol mixture and the active agent is azaline B. In each of these embodiments, the result was a single continuous phase in which both the polymer and active agent were solubilized, thereby avoiding prior art processes which are characterized by two or more phases. The solvents and/or non-solvents can be added in a wide range of relative amounts, including for example about 1:10 to about 10:1 or about 1:3 to about 3:1, by volume, as is appropriate.

After the polymer/active agent solution is formed it can be processed to form microdroplets. These microdroplets can then be frozen by means suitable to form microparticles. Examples of means for processing the polymer/active agent solution to form droplets include directing the solution through an ultrasonic nozzle, pressure nozzle, Rayleigh jet, or by other means known for creating droplets from solution such as those described in U.S. Pat. No. 5,019,400, issued to Gombotz et al., U.S. Pat. No. 5,922,253, issued on Jul. 13, 1999 and U.S. Pat. No. 5,817,343, issued Oct. 6, 1998, the teachings of all of which are incorporated herein by reference in their entirety.

The microdroplets are then frozen by means suitable to form microparticles. Means suitable for freezing droplets to form microparticles include directing the droplets into or near a liquified gas, such as liquid argon and liquid nitrogen to form frozen microdroplets which are then separated from the liquid gas. The frozen microdroplets are then exposed to an extraction solvent or curing solvent or phase, which is generally a poor solvent for the polymer, which has a lower melting point than the continuous phase and which has sufficient miscibility with the continuous phase to extract solid and/or thawed continuous phase from a frozen microparticle.

In one method the liquified gas overlays frozen extraction solvent, as described in U.S. Pat. No. 5,019,400, issued to Gombotz et al., the entire content of which is incorporated herein by reference. In a second method, the liquified gas and cold extraction solvent are maintained in a distinct "freezing zone" and "extraction zone," as described in co-pending U.S. patent application Ser. No. 08/443,726, filed May 18, 1995, the content of which is incorporated herein in its entirety. As stated above, the purpose of the extraction solvent is to remove or extract, as solid and/or a liquid, any continuous phase in the frozen microdroplets, thereby forming active agent containing microparticles. Typically, the extraction solvent or curing phase is selected from one or more of the polymer non-solvents discussed above. It can be the same or different as any polymer non-solvent employed in the continuous phase, as described herein. It can optionally further include an active agent non-solvent as well. Typical extraction solvents include, for example, ethanol, methanol, ethyl ether, alkanes such as pentane, isopentane, hexane, heptane, and oils such as mineral oils, fish oils, silicone oil, vegetable oils, or combinations thereof. Vegetable oils, such as olive oil, sesame oil, soybean oil, safflower oil, peanut oil, cottonseed oil, coconut oil, palm oil or combinations thereof, are preferred. It is generally desirable that the extraction solvent(s) or curing phase possess a melting point the same or, preferably, lower than the continuous phase. Thus, the extraction step can be conducted or initiated at a temperature at which the extraction solvent(s) or curing phase is a liquid and the microdroplets (including the continuous phase) are frozen. Mixing ethanol with other suitable extraction solvents, such as an alkane, including hexane, heptane or pentane, can directly impact the encapsulation efficiency, morphology, and consistency therein of the resulting microspheres as well as cause an unexpected increase in the rate of solvent extraction, above that achieved by ethanol alone, from certain polymers, such as poly(lactide-co-glycolide) polymers.

In another method the polymer/active agent matrix, as formed above, is fragmented at a temperature below the glass transition temperature of the polymer/active agent matrix, thereby forming polymer/active agent microparticles, as described in co-pending U.S. patent application Ser. No. 08/649,128, filed May 14, 1996 the entire teachings of which are incorporated herein by reference in their entirety.

A wide range of sizes of polymer-based sustained release devices can be made by varying the droplet size, for example, by changing the ultrasonic nozzle frequency or diameter. If larger devices are desired, the polymer/active agent solution can be processed by passage through a syringe or the like directly into the cold liquid. Alternatively, the solution can be dripped or otherwise added to the cold liquid. Increasing the viscosity of the polymer/active agent solution can also increase device size. The size of the devices which can be produced by the method of the invention are, for example, microparticles ranging from greater than about 1000 to about 1 micrometer in diameter.

The term "polymer-based sustained release device," as defined herein, comprises a polymer and an active agent (also refereed to herein as a "polymer/active agent matrix"). The polymers of the present invention are generally biocompatible. Suitable biocompatible polymers can be either biodegradable or non-biodegradable polymers, or blends or copolymers thereof.

A polymer is biocompatible if the polymer, and any degradation products of the polymer, are substantially non-toxic to the recipient, and also presents no unacceptable, deleterious or untoward effects on the recipient's body, such as a significant immunological reaction at the site of administration.

Biodegradable, as defined herein, means the composition will degrade or erode in vivo to form smaller chemical species which are biometabolizable and/or excretable. Degradation can result, for example, by enzymatic, chemical and/or physical processes. Suitable biocompatible, biodegradable polymers include, for example, poly(lactides), poly (glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly (dioxanone)s, poly(alkylene alkylates)s, copolymers of polyethylene glycol and polyorthoesters, biodegradable polyurethanes, blends and copolymers thereof.

Biocompatible, non-biodegradable polymers suitable for a sustained release device include non-biodegradable polymers selected from the group consisting of polyacrylates, polymers of ethylene-vinyl acetates and acyl substituted cellulose acetates, non-degradable polyurethanes, polystyrenes, polyvinyl chloride, polyvinyl fluoride, poly (vinyl imidazole), chlorosulphonate polyolefins, polyethylene oxide, blends and copolymers thereof.

Further, the terminal functionalities or pendant groups of the polymers can be modified, for example, to modify hydrophilicity, hydrophobicity and/or provide, remove or block moieties which can interact with the active agent (via, for example, ionic or hydrogen bonding).

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is between about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA").

The term "active agent," as defined herein, is an agent, or its pharmaceutically acceptable salt, which when released in vivo, possesses the desired biological activity, for example therapeutic, diagnostic and/or prophylactic properties in vivo. Examples of suitable biologically active agents include proteins such as immunoglobulins, antibodies, cytokines (e.g., lymphokines, monokines, chemokines), interleukins, interferons, erythropoietin, nucleases, tumor necrosis factor, colony stimulating factors, insulin, enzymes (e.g. superoxide dismutase, a plasminogen activator), tumor suppressors, blood proteins, hormones and hormone analogs (e.g., growth hormone, adrenocorticotropic hormone, luteinizing hormone releasing hormone (LHRH) and azaline B), vaccines (e.g., tumoral, bacterial and viral antigens), antigens, blood coagulation factors; growth factors; peptides such as protein inhibitors, protein antagonists, and protein agonists; nucleic acids, such as antisense molecules; oligonucleotides; and ribozymes. Small molecular weight agents suitable for use in the invention include, antitumor agents such as bleomycin hydrochloride, methotrexate and adriamycin; antibiotics such as gentamicin, tetracycline hydrochloride and ampicillin; antipyretic, analgesic and anti-inflammatory agents; antitussives and expectorants such as ephedrine hydrochloride, methylephedrine hydrochloride, noscapine hydrochloride and codeine phosphate; sedatives such as chlorpromazine hydrochloride, prochlorperazine hydrochloride and atropine sulfate; muscle relaxants such as tubocurarine chloride; antiepileptics such as sodium phenytoin and ethosuximide; antiulcer agents such as metoclopramide; antidepressants such as clomipramine; antiallergic agents such as diphenhydramine; cardiotonics such as theophillol; antiarrhythmic agents such as propranolol hydrochloride; vasodilators such as diltiazem hydrochloride and bamethan sulfate; hypotensive diuretics such as pentolinium and ecarazine hydrochloride; antidiuretic agents such as metformin;

anticoagulants such as sodium citrate and sodium heparin; hemostatic agents such as thrombin, menadione sodium bisulfite and acetomenaphthone; antituberculous agents such as isoniazide and ethanbutol; hormones such as prednisolone sodium phosphate and methimazole; and narcotic antagonists such as nalorphine hydrochloride.

The amount of active agent which is contained in the polymer-based sustained release device is a therapeutically or prophylactically effective amount which can be determined by a person of ordinary skill in the art taking into consideration factors such as body weight, condition to be treated, type of device used, and release rate from the device.

A polymeric drug delivery device of the invention can contain from about 0.01% (w/w) to about 90% (w/w) of active agent (total weight of polymer/active agent). The amount of agent can vary depending upon the desired effect of the agent, the planned release levels, and the time span over which the agent is to be released. A low range of agent loading can be from about 0.1% (w/w) to about 30% (w/w). In treatments where a low range of agent loading is desired a preferred range is from about 0.5% (w/w) to about 20% (w/w). A high range of agent loading is that greater than or equal to about 50%. In treatments where a high range of agent loading is employed a preferred range is from about 50% (w/w) to about 85% (w/w) and more preferably from about 50% (w/w) to about 70% (w/w).

A sustained release of active agent is a release which occurs over a period of time longer than that which would be obtained following similar administration of the active agent as a dispersion or solution in a carrier. Generally, the sustained release device can deliver the active agent for at least about seven days and, preferably, up to about three months.

The polymer-based sustained release device of this invention can be formed into many shapes such as a film, a pellet, a cylinder, a wafer, a disc or a microparticle. A microparticle, generally has a diameter of less than about one millimeter. A microparticle can have a generally spherical, non-spherical or irregular shape. Typically, the microparticle will be of a size suitable for injection. A preferred size range for microparticles is from about 1 to about 250 microns in diameter. The sustained release device in the form of a wafer or disc, for example, will typically be of a size suitable for implantation and, for example, can be manufactured by compressing microparticles.

The present invention can be used to incorporate and deliver a wide variety of active agents. Most often, the composition of the present invention will be used to deliver an active agent to a human or other animal for purposes of therapy, prophylaxis, hygiene, analgesics, cosmetics or the like. Such uses where the compositions are delivered to a human or other animal will generally be referred to as in vivo uses. The composition of the present invention will also have in vitro uses where an active substance is being delivered to an environment or system other than a human or animal such as in the sustained release of agrochemicals or in diagnostics. One of the major in vivo uses for the composition of the present invention will be for the delivery of drugs and other pharmaceutical agents in human and veterinary applications. For both in vivo and in vitro uses, the compositions will deliver the active substance to a surrounding environment.

Figure 2:
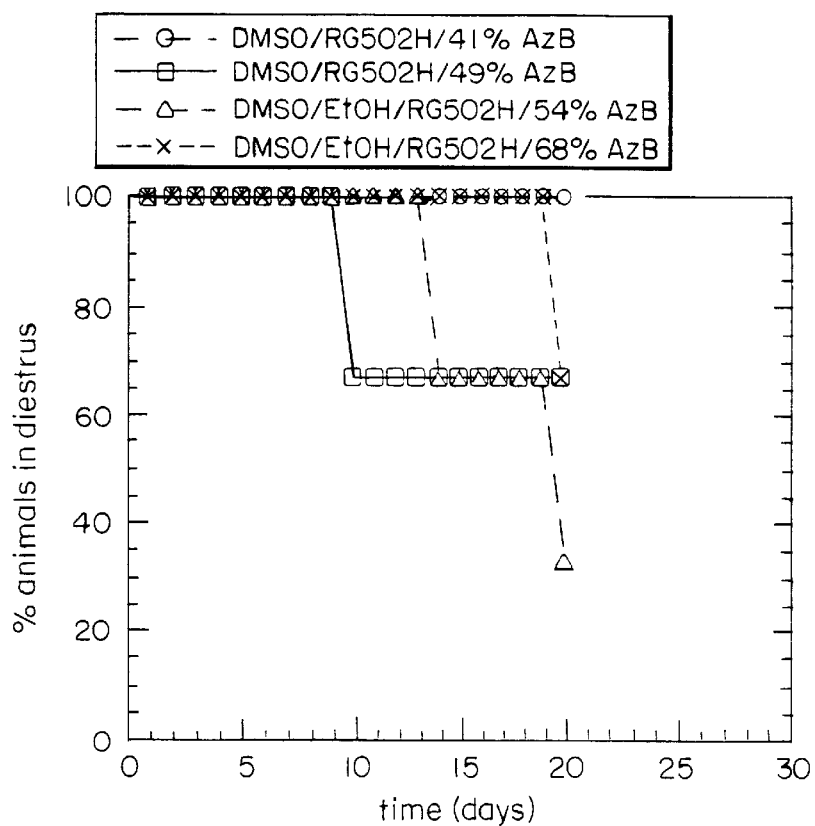
FIG. 2 is a plot of the percent of animals per treatment group in diestrus for groups of rats treated with microparticles having the indicated load of azaline B prepared using the method of the invention, according to Examples 1 and 3, as described herein, and having the indicated load of azaline B, versus time.

Unexpectedly, the above process resulted in the ability to form sustained delivery devices even at very high loads (greater than or equal to at least about 50% (w/w)) with improved release characteristics and duration of release, as illustrated, for example, in FIGS. 1 and 2. It was also found that the morphology of the device changed with the amount, or load, of the active agent. The device, or microparticle, was porous at low loads (e.g, 10% to 30%), similar to the microparticles obtained in the known processes. However, at high loads (e.g. 50% to 90%), the microparticles were dense. Thus, the invention includes microparticles or sustained release devices manufactured by the process of the invention.

The invention also includes an improved sustained release device which has incorporated therein an amount of active agent greater than or equal to at least about 50% by weight (w/w) of the polymer-based sustained release device (also referred to as a "high load"). A preferred range is from about 50% (w/w) to about 85% (w/w) and more preferably from about 50% (w/w) to about 70% (w/w). In general, these high load microparticles are difficult to manufacture employing the prior art processes and the high encapsulation efficiency observed is unexpected. In addition, the high load microparticles would not be expected to exhibit improved sustained release of active agent over lower active agent loads. In a specific embodiment, the polymer-based sustained release device has a high load of azaline B. In a more specific embodiment, the polymer of the sustained release device is poly(lactide-co-glycolide) having a high load of azaline B.

In a further embodiment, the improved polymer-based sustained release device has an increased period of sustained release and/or increased bioavailability over that achieved with a device prepared by a method which does not solubilize the active agent in the polymer solution. For example, when microparticles containing azaline B are prepared employing methylene chloride as the sole polymer solvent the active agent is not solubilized (referred to herein as the "Particulate Method"). Comparison of active agent release from these microparticles with those prepared employing DMSO as the continuous phase (active agent solubilized) can be achieved by comparing FIGS. 1 and 2. Clearly, the polymer-based sustained release devices prepared by the process wherein the active agent is solubilized (FIG. 2), demonstrate an increased period of sustained release over those devices wherein a single polymer solvent which does not solubilize the active agent is employed (FIG. 1).

Without being bound by a particular theory it is believed that the release of the biologically active agent can occur by at least two different mechanisms. First, release can occur due to degradation of the polymer. Second, biologically active agent can be released by diffusion through the channels generated in the polymer-based sustained release device, such as by the dissolution of the active agent or by voids or pores created by the removal of the polymer/active agent solvent during the synthesis of the drug delivery device.

The rate of degradation can be controlled by changing polymer properties that influence the rate of hydration and/or degradation of the polymer. These properties include, for instance, the ratio of different monomers, such as lactide and glycolide, comprising a polymer; the use of the L- or D-isomer or racemic mixture of a chiral monomer; a polymer, such as a poly(lactide-co-glycolide) polymer that has, for instance, a hydrophobic or a hydrophilic end group; the morphology of the particle as impacted for example, by choice of solvents for polymer during preparation; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

In addition, the active agent in the sustained release device of the present invention can also contain other excipients, such as stabilizers, bulking agents or aggregation-stabilizing agents. Stabilizers are added to maintain the potency of the biologically active agent during device fabrication, storage and over the duration of the agent's release. Suitable stabilizers include, for example, carbohydrates, amino acids, fatty acids and surfactants which are known to those skilled in the art. For amino acids, fatty acids and carbohydrates, such as sucrose, lactose, mannitol, inulin, maltose, dextran and heparin, the mass ratio of carbohydrate to biologically active agent is typically between about 1:10 and about 20:1. For surfactants, such as polysorbates (e.g., Tween™) and poloxamers and poloxamines (e.g., Pluronic™), the mass ratio of surfactant to agent is typically between about 1:1000 and about 1:2.

Aggregation-stabilizing agents are agents which stabilize the biologically active agent against significant aggregation in vivo over the sustained release period. Typically an aggregation stabilizer reduces the solubility of the biologically active agent, precipitates out a salt of the agent or forms a complex of the agent. The aggregation stabilizer and the biologically active agent can be separately contained within the drug delivery device, such as a device containing particles of aggregation stabilizer and separate particles of biologically active agent, and/or can be combined together in complexes or particles which contain both the aggregation stabilizer and the biologically active agent.

The use of aggregation-stabilizing agents is also described in U.S. Pat. No. 5,716,644 issued on Feb. 10, 1998 and U.S. Pat. No. 5,674,534, issued on Oct. 7, 1997 and, U.S. patent application Ser. No. 08/521,744, filed on Aug. 31, 1995, the teachings of which are incorporated herein by reference in their entirety.

Metal cations can be suitable as aggregation-stabilizing agents. These metal cations include cations of transition metals, such as $Zn^{+2}$, $Cu^{+2}$, $Co^{+2}$, $Fe^{+3}$ and $Ni^{+2}$. The use of metal cations as aggregation-stabilizing agents, is also described in U.S. Pat. No. 5,711,968, issued on Jan. 27, 1998, U.S. patent application Ser. No. 08/521,744, filed Aug. 31, 1995, PCT Patent Application PCT/US95/07348, filed Jun. 7, 1995, U.S. Pat. No. 5,654,010 issued to Johnson et al. and U.S. Pat. No. 5,667,800 issued to Johnson et al., the teachings of which are incorporated herein by reference in their entirety.

The polymer-based sustained release device can also contain a metal cation component which is dispersed within the polymer. This metal cation component acts to modulate the release of biologically active agent from the polymeric matrix.

A metal cation component used in modulating release typically contains at least one type of multivalent metal cation. Examples of metal cation components suitable to modulate release of biologically active agent, include, or contain, for instance, $Mg(OH)_2$, $MgCO_3$ (such as $4MgCO_3 \cdot Mg(OH)_2 5H_2O$), $ZnCO_3$ (such as $3Zn(OH)_2 2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)$ A suitable ratio of metal cation component-to-device is between about 1:99 to about 1:1 by weight. The optimum ratio depends upon the polymer and the metal cation utilized.

A polymeric matrix containing a dispersed metal cation component to modulate the release of a biologically active agent from the polymeric matrix is further described in U.S. Pat. No. 5,656,297 issued to Bernstein et al. and co-pending PCT Patent Application PCT/US95/05511, the teachings of which are incorporated herein by reference in their entirety.

In a third aspect, the present invention provides a method of using the polymer-based sustained release device comprising providing a sustained delivery rate of active agent, in a subject, over a therapeutically useful period of time, by administering to the subject a dose of said polymer-based sustained release device.

The sustained release device of this invention can be administered to a human, or other animal, by injection, implantation (e.g, subcutaneously, intramuscularly, intraperitoneally, intracranially, intraocularly, intravaginally and intradermally), administration to mucosal membranes (e.g., intranasally or by means of a suppository), or in situ delivery (e.g. by enema or aerosol spray) to provide the desired dosage of an agent based on the known parameters for treatment with that agent of the various medical conditions.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The invention will now be further and specifically described by the following examples.

EXEMPLIFICATION METHODS

The polymers employed in the following examples are described below:

Purchased from Boehringer Ingelheim
    RG 502H: 10K MW, 50:50 Poly(D,L-lactide-co-glycolide) (PLGA), hydrophilic end groups
    RG 501H: 5K MW, 50:50 Poly(D,L-lactide-co-glycolide) (PLGA), hydrophilic end groups
    R 104: 5K MW, Poly(D,L-lactide)

Purchased from Birmingham Polymers, Inc., Birmingham Ala.
    Lot 112-43-1: 5K MW, Poly(D,L-lactic acid)

EXAMPLE 1

POLYMER SOLVENT METHOD

A polymer/active agent solution can be formed by dissolving an appropriate amount of polymer and active agent in a continuous phase comprising one or more polymer solvents which also solubilize the active agent. If more than one polymer solvent is employed both need not solubilize the active agent. The polymer/active agent solution can then be atomized into droplets which can be frozen. The solvent is then removed from the frozen droplets to form a polymer/active agent matrix by diffusion of the polymer solvent into a polymer non-solvent phase, the cure phase. The cure phase can be comprised of a single solvent or a mixture of solvents. The particles are collected from the polymer non-solvent by filtration and residual polymer solvent and non-solvent are removed by evaporation. The dry product is sieved through an appropriately sized mesh so as to produce an injectable product.

The process can be summarized as follows:

Formation of a polymer/active agent solution by dissolving PLGA copolymer (3–28%(w/v)) and active agent in DMSO.

Atomization of the polymer active agent solution by sonication, and freezing of the droplets by contact with liquid nitrogen.

Extraction of the polymer/active agent solvent in 80° C. ethanol cure solvent, thereby forming a polymer active agent matrix.

Isolation of the particles from the cure solvent by filtration.

Removal of remaining solvents by evaporation.

Sizing of particles by passage through an appropriately sized mesh so as to produce an injectable product.

Figure 3:
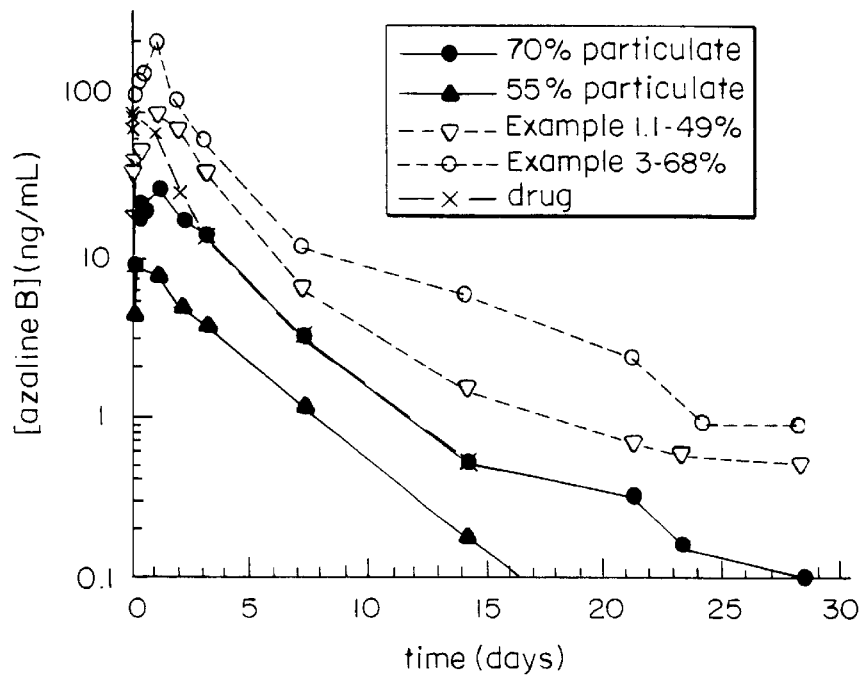
FIG. 3 is a plot of serum concentrations (ng/ml) of azaline B for groups of animals treated with azaline B containing microparticles prepared by using the Particulate Method and the method of the invention, according to Examples 1 and 3, as described herein, and having the indicated load of azaline B, versus time.

The "Particulate Method," referred to in FIGS. 1 and 3, is a process similar to that summarized above, but where the active agent is added to the polymer solution as a solid and remains in the solid or particulate form (i.e., does not dissolve) throughout the process.

EXAMPLE 1.1

63% (w/w) PEPT-DE LOADED, PLGA MICROPARTICLES, ETHANOL CURE PHASE

High load microparticles comprising PLGA and azaline B were prepared as follows:

1) A solution comprising DMSO (0.701 ml), PLGA (0.043 g) (10K MW, hydrophilic end groups) and azaline B acetate (0.185 g) was prepared by mixing the components at room temperature.
2) The solution from step 1 was atomized by an ultrasonic atomizing probe (Sonics & Materials #630-0507) at a constant flow rate of 0.3 ml/minute.
3) The atomized droplets were frozen upon passage through a cold nitrogen gas phase and then into liquid nitrogen. The liquid nitrogen layer was placed over a frozen non-solvent phase (100% ethanol).
4) The liquid nitrogen layer containing the frozen droplets was allowed to evaporate at −80° C. and the polymer/active agent solvent (DMSO) was extracted from the frozen droplets over an 18 hour incubation time at −80° C. employing ethanol as the cure phase.
5) The microparticles were separated from the cure phase by filtration and freeze-dried.
6) The dry product was sieved through a 180 $\mu$m mesh sieve.

EXAMPLE 1.2

63% (w/w) PEPTIDE LOADED, PLGA MICROPARTICLES, HEPTANE/ETHANOL CURE PHASE

1) A solution comprising DMSO (50.0 ml) and PLGA (5.0 g)(10K MW, hydrophilic end groups) copolymer was prepared at room temperature. To 3.0 ml of the polymer solution was added 0.233 g of azaline B acetate, and allowed to dissolve.
2) The solution from step 1 was atomized by an ultrasonic atomizing probe (Sonics & Materials #630-0507) at a constant flow rate of 0.3 M1/minute.
3) The atomized droplets were frozen upon passage through a cold nitrogen gas phase and then into liquid nitrogen. The liquid nitrogen layer was placed over a frozen non-solvent phase (75% heptane; 25% ethanol, v/v).
4) The liquid nitrogen layer containing the frozen droplets was allowed to evaporate at −80° C. The frozen non-solvent phase was allowed to melt at −80° C. and the polymer/active agent solvent (DMSO) was extracted from the frozen droplets over an 18 hour incubation time at −80° C. employing a mixture of heptane/ethanol (75:25) as the cure phase.
5) The microparticles were separated from the cure phase by filtration and freeze-dried.
6) The dry product was sieved through a 180 $\mu$m mesh sieve.

Microparticles containing a 49% and a 41% load of azaline B (FIG. 3) were also prepared employing the process of Example 1.1.

EXAMPLE 2

POLYMER SOLVENT/POLYMER NON-SOLVENT

The general procedure for the formation of microparticles using a mixture of polymer solvent/polymer non-solvent, is similar to the Polymer Solvent Method, described above, with the exception that the continuous phase comprises a polymer solvent/polymer non-solvent mixture. This method provides for the solubilization of active agents such as tRNA and ovalbumin, which are not readily soluble in polymer solvents. In the example described below the polymer non-solvent employed was water.

The polymer solvent/water mixture was formulated such that the addition of water to the system increased the solubility of the active agent, but did not exceed the concentration at which substantial precipitation of the polymer would result. In addition, the polymer non-solvent can be used to predissolve the active agent; the resulting solution can then be added to the polymer solution such that a transient continuous phase results. The transient continuous phase can be further processed prior to precipitation of the active agent or polymer.

A specific example of this method is the manufacture of a device comprising D,L-PLA (100% D,L-Poly(lactic acid), 5K MW) and ovalbumin at a 1% (w/w) load.

1) A 5% (w/v) D,L-PLA solution was prepared by dissolving D,L-PLA in DMSO at 50 mg D,L-PLA per ml of DMSO.
2) The active agent ovalbumin was dissolved in deionized water at a concentration of 100 mg/ml. 20 microliters of the aqueous solution was added to 39.6 ml of the polymer solution in a dropwise manner, with mixing.
3) The solution from step 2 was atomized by an air atomization. The atomized droplets are collected in a −70° C. cure phase (ethanol), resulting in formation of the polymer matrix, with drug distributed throughout.
4) The microparticles were separated from the cure phase by filtration and freeze-dried.
5) The dry product was sieved through a 180 $\mu$m mesh sieve.

EXAMPLE 3

POLYMER SOLVENT/POLYMER NON-SOLVENT

The general procedure for the formation of microparticles using a mixture of a polymer solvent and a polymer non-solvent, is similar to the Polymer Solvent Method, described in detail above, with the exception that the continuous phase is comprised of a polymer solvent and a polymer non-solvent, for example, DMSO and ethanol. It is understood that the polymer non-solvent in this example is also an active agent non-solvent.

A specific example of this method is the manufacture of a sustained release device comprising PLGA and azaline B acetate at a 60% (w/w) load.

1) A 10% (w/v) solution of PLGA copolymer (10K MW, hydrophilic end groups) in a mixture of DMSO/ethanol (75:25 v/v) was prepared.

2) Azaline B acetate, in dry powder form was dissolved in the polymer solution at approximately room temperature to give a final concentration of 0.233 g of azaline B acetate per ml of polymer solution.
3) The solution from step 2 was atomized by an ultrasonic atomizing probe (Sonics & Materials #630-0507) at a constant flow rate of 0.3 ml/minute.
4) The atomized droplets were frozen upon passage through a cold nitrogen gas phase and then into liquid nitrogen. The liquid nitrogen layer was placed over a frozen non-solvent phase (100% ethanol).
5) The liquid nitrogen layer containing the frozen droplets was allowed to evaporate at −80° C. The frozen non-solvent phase was allowed to melt at −80° C. and the polymer solvent/active agent non-solvent (DMSO/ethanol) was extracted from the frozen droplets over an 18 hour incubation time at −80° C. employing ethanol as the cure phase.
6) The microparticles were separated from the cure phase by filtration and freeze-dried.
7) The dry product was sieved through a 180 μm mesh sieve.

Microparticles containing a 54% and a 68% load of azaline B (depicted in FIG. 2) were also prepared employing this process.

EXAMPLE 4

POLYMER SOLVENT/ACTIVE AGENT NON-SOLVENT (OLIVE OIL CURE PHASE)

The general procedure for the formation of microparticles using a mixture of polymer solvent/active agent non-solvent, is similar to the Polymer Solvent Method, described in detail above, with the exception that the continuous phase comprises a polymer solvent/active agent non-solvent.

A specific example of this method, is the preparation of a sustained release device comprising PLGA and azaline B at a load 70% (w/w) active agent.

1) A 10% (w/v) solution of PLGA copolymer (10K MW, hydrophilic end groups) in a mixture of DMSO/acetone (80:20 v/v) was prepared.
2) Azaline B acetate, in dry powder form was dissolved in the polymer solution at room temperature to give a final concentration of 0.233 g of azaline B per ml of polymer solution.
3) The solution resulting from step 2 was atomized by an ultrasonic atomizing probe (Sonics & Materials #630-0507) at a constant flow rate of 0.3 ml/minute.
4) The atomized droplets were frozen upon contact with cold (4° C.) olive oil.
5) The polymer solvent/active agent non-solvent (DMSO/acetone) was extracted from the frozen droplets over a 7 day incubation time at 4° C., with mixing.
6) The microparticles were separated from the oil by the formation of an emulsion in which the oil phase containing the microspheres was rapidly mixed with a 4×volume of a heptane/ethanol mixture (75:25 v/v). The microparticles were separated from the emulsion phase by filtration. The emulsion/filtration procedure was repeated 3 times.
7) The microparticles were separated from the final emulsion phase by filtration and freeze-dried.
8) The dry product was sieved through a 180 μm mesh sieve.

EXAMPLE 4.1

POLYMER SOLVENT/ACTIVE AGENT NON-SOLVENT-65% (w/w) LOAD (HEPTANE/ETHANOL 75:25 CURE PHASE)

1) A 10% (w/v) PLGA copolymer solution was prepared by dissolving PLGA copolymer (10K MW, hydrophilic end groups) in a mixture of DMSO/acetone (80:20 v/v).
2) Azaline B acetate, in dry powder form was dissolved in the polymer solution at room temperature to give a final concentration of 0.233 g of azaline B per ml of polymer solution.
3) The solution resulting from step 2 was atomized by an ultrasonic atomizing probe (Sonics & Materials #630-0507) at a constant flow rate of 0.3 ml/minute.
4) The atomized droplets were frozen upon passage through a cold nitrogen gas phase and then into liquid nitrogen. The liquid nitrogen layer was placed over a frozen non-solvent phase (75:25% v/v heptane:ethanol).
5) The liquid nitrogen layer containing the frozen droplets was allowed to evaporate at −80° C. The frozen non-solvent phase was allowed to melt at −80° C. and the polymer solvent/active agent non-solvent (DMSO/acetone) was extracted from the frozen droplets over an 18 hour incubation time at −80° C. employing a mixture of heptane/ethanol (75:25) as the cure phase.
6) The microparticles were separated from the non-solvent phase by filtration and freeze-dried.
7) The dry product was sieved through a 180 μm mesh sieve.

EXAMPLE 4.2

POLYMER SOLVENT/ACTIVE AGENT NON-SOLVENT-68% (w/w) LOAD (ETHANOL CURE PHASE)

1) A 10% (w/v) PLGA copolymer solution was prepared by dissolving PLGA copolymer (10K MW, hydrophilic end groups) in a mixture of DMSO/acetone (80:20 v/v).
2) Azaline B acetate, in dry powder form was dissolved in the polymer solution at room temperature to give a final concentration of 0.233 g of azaline B per ml of polymer solution.
3) The solution resulting from step 2 was atomized by an ultrasonic atomizing probe (Sonics & Materials #630-0507) at a constant flow rate of 0.3 ml/minute.
4) The atomized droplets were frozen upon passage through a cold nitrogen gas phase and then into liquid nitrogen. The liquid nitrogen layer was placed over a frozen non-solvent phase (ethanol).
5) The liquid nitrogen layer containing the frozen droplets was allowed to evaporate at −80° C. The frozen non-solvent phase was allowed to melt at −80° C. and the polymer solvent/active agent non-solvent (DMS0/acetone) was extracted from the frozen droplets over an 18 hour incubation time at −80° C. employing ethanol as the cure phase.
6) The microparticles were separated from the non-solvent phase by filtration and freeze-dried.
7) The dry product was broken up by a gentle, manual grinding and passed through a 180 μm mesh sieve.

EXAMPLE 5

MANUFACTURE OF STERILE PRODUCT USING THE "MICROPARTICULATE METHOD"-POLYMER SOLVENT/ACTIVE AGENT NON-SOLVENT

The method can be used to produce sterile product by enabling the sterile filtration (0.2 μm) of the polymer/active agent solution, prior to further processing.

For example, the manufacture of a sterile 15% (w/w) loaded azaline B acetate/PLGA formulation was performed as follows:

1) A 20% (w/v) solution of PLGA copolymer (10K MW, hydrophilic end groups) in dichloromethane was prepared by dissolving 0.2 g of PLGA per ml of dichloromethane. The polymer solution (639 ml) was introduced into a sterile vessel, equipped with a rotor-stator homogenizer, using 0.22 µm filtration. The polymer solution was chilled to approximately −77° C.

2) Azaline B was dissolved in DMSO at a concentration of 12.5% (w/w) by dissolving 0.125 g of azaline B per gram of DMSO.

3) 135 g of the azaline B solution was introduced slowly into the sterile tank containing the polymer solution via 0.22 µm filtration. The rotor-stator homogenizer was run immersed in the polymer solution and the temperature was maintained at approximately −77° C. during the addition of the azaline B/DMSO solution.

4) The DMSO/azaline B solution freezes upon introduction to the cold polymer solution and is dispersed throughout the dichloromethane polymer solution by action of the rotor-stator homogenizer. As the DMSO and dichloromethane mix, peptide precipitates as a microsuspension.

5) The resulting microsuspension was atomized by air atomization and the droplets frozen by contact with liquid nitrogen.
6) The frozen droplets were mixed with an excess volume of ethanol upon which the DMSO and the dichloromethane were extracted to produce a polymer matrix with the active agent dispersed throughout.

The following Table summarizes the PLGA microparticles, prepared according to Examples 1 through 5. % Load and Encapsulation Efficiency were determined by analysis of the nitrogen content of the microparticles using a CE-440 Elemental Analyzer available from Exeter Analytical, Inc., Lowell, Mass.

In Vivo Data

EXAMPLE 6

RAT ESTROUS MODEL

The Rat Estrous Cyclicity Model is described in detail in Hahn et al., Biological Assays Utilized to Characterize LHRH and its Analogs. In: *LHRH and its Analogs, Contraception and Therapeutic Applications* (Eds. Vickery B H, Nestor J J, and Hafez ESE), pp. 49–60. MTP Press Ltd, Lancaster, England, 1984, the contents of which are incorporated herein by reference. The model is used to assess the pharnacodynamic effect which an effective serum level of azaline B (at least 2.0 ng/ml), provided by the administration of a sustained release device of the invention, has on the estrous cycle of the rat. When the minimum effective concentration of azaline B is present in serum, the estrus phase of the estrous cycle of the rat is suppressed and the rat remains in the diestrus phase of the estrous cycle.

Microparticles containing an effective amount of azaline B were prepared according to the "Particulate Method," described above, and the methods of Examples 1 and 3. The presence of azaline B activity was measured as the percent of a test group which remained in the diestrus phase of the estrous cycle. Animals were subcutaneously injected with equal amounts of azaline B either encapsulated in a microparticle or unencapsulated. The injections employed a vehicle of 3% carboxymethyl cellulose (low viscosity) and 1% Tween-20 in saline. The results are depicted in FIGS. 1 and 2 which show a plot of the percent of animals per treatment group in diestrus for each formulation evaluated versus time. FIG. 1 show that rats treated with the particulate formulations, were observed to begin cycling after 8–10 days. The rats treated with the microparticles prepared according to the method of the invention, specifically Examples 1 and 3, as shown in FIG. 2 had a further delay in the onset of cycling, indicating the presence of an effective serum concentration for a longer period of time.

EXAMPLE 7

EVALUATION OF AZALINE B SERUM LEVELS

Microparticles were processed using the "Particulate Method" described above and the methods of Examples 1 and 3. Animals were subcutaneously injected with equal amounts of azaline B either encapsulated in a microparticle or unencapsulated. The injections employed a vehicle of 3% carboxymethyl cellulose (low viscosity) and 1% Tween-20

| Example | Polymer/ Active Phase | Process | Freeze Phase | Cure Phase | Product | Load (% w/w) | Encapsulation Efficiency (% Target) |
|---|---|---|---|---|---|---|---|
| 1.1 | DMSO | Atomization | Liquid Nitrogen | −80° C. Ethanol | Microparticles | 63 | 90 |
| 1.2 | DMSO | Atomization | Liquid Nitrogen | −80° C. Heptane/Ethanol 75:25 | Microparticles | 63 | 90 |
| 2 | DMSO/ Water | Atomization | Ethanol (<0° C.) | −80° C. Ethanol | Microparticles | 1 | 67 |
| 3 | DMSO/ Ethanol | Atomization | Liquid Nitrogen | −80° C. Ethanol | Microparticles | 60 | 85 |
| 4 | DMSO/ Acetone | Atomization | Liquid Nitrogen | 4° C. Olive Oil | Microparticles | 70 | 100 |
| 4.1 | DMSO/ Acetone | Atomization | Liquid Nitrogen | −80° C. Heptane/Ethanol 75:25 | Microparticles | 65 | 93 |
| 4.2 | DMSO/ Acetone | Atomization | Liquid Nitrogen | −80° C. Ethanol | Microparticles | 68 | 97 |
| 5 | Methylene Chloride/ DMSO | Atomization "Micro-particulate" | Liquid Nitrogen | −80° C. Ethanol | Microparticles | 15 (Sterile) | 100 | in saline. Serum levels (ng/ml) were determined at various times over a 28 day period and the results are show in FIG. 3 as a plot of the concentration of azaline B (ng/ml), versus time. Serum levels were determined using an electrochemiluminescent immunoassay method. In this method quantitation is performed using an antibody that is specific for azaline B, and concentration is determined by comparison to a standard curve.

Briefly, the animals were anesthetized with halothane and blood samples were collected via a lateral tail vein. The blood was clotted at room temperature, centrifuged at approximately 6000×g for about five minutes and stored at −70° C. until analysis could be performed.

FIG. 3 is a graph of the serum levels of azaline B versus time. The Figure demonstrates that the release profile of high load microparticles prepared according the methods of Examples 1 and 3 was improved over that seen with microparticles prepared according to the "Particulate Method."

While this invention has been particularly shown and described with references to preferred embodiments thereof, it will be understood by those skilled in the art that various changes in form and details may be made therein without departing from the scope of the invention encompassed by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for forming a polymer-based sustained release device comprising the steps of:
    a) forming a polymer/biologically active agent solution by mixing a polymer, an effective amount of the biologically active and a continuous phase comprising a polymer solvent/polymer non-solvent mixture wherein the polymer and biologically active agent are present in relative concentrations such that the device contains about 50% by weight or more of the biologically active agent and the amount of non-solvent achieves solubilization of the biologically active agent and does not cause substantial precipitation of the polymer;
    b) forming droplets of the polymer/biologically active agent solution;
    c) freezing the droplets of the polymer/biologically active agent solution; and
    d) removing the continuous phase of step (a) from the polymer/biologically active agent solution, thereby forming a solid polymer/biologically active agent matrix.

2. The method of claim 1 wherein the polymer solvent is DMSO.

3. The method of claim 2 wherein the polymer non-solvent is ethanol.

4. The method of claim 1 wherein the droplets are microdroplets.

5. The method of claim 1 wherein the active agent is a peptide, an antigen or a small molecule drug.

6. The method of claim 1 wherein the active agent is an LHRH analog.

7. The method of claim 6 wherein the LHRH analog is azaline B.

8. The method of claim 1 wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

9. A method for forming a polymer-based sustained release device comprising the steps of:
    a) forming a polymer/biologically active agent solution by mixing a polymer, an effective amount of the biologically active agent and a continuous phase comprising a polymer solvent/biologically active agent non-solvent mixture wherein the amount of non-solvent achieves solubilization of the biologically active agent and does not cause substantial precipitation of the polymer;
    b) forming droplets of the polymer/biologically active agent solution;
    c) freezing the droplets of the polymer/biologically active agent solution; and
    d) removing the continuous phase of step (a) from the polymer/biologically active agent solution, thereby forming a solid polymer/biologically active agent matrix.

10. The method of claim 9 wherein the droplets are microdroplets.

11. The method of claim 9 wherein the active agent is a peptide, an antigen or a small molecule drug.

12. The method of claim 9 wherein the active agent is an LHRH analog.

13. The method of claim 12 wherein the LHRH analog is azaline B.

14. The method of claim 9 wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

15. A method for forming a polymer-based sustained release device comprising the steps of:
    a) forming a polymer/biologically active agent solution by mixing a polymer, an effective amount of the biologically active agent, and a continuous phase comprising a polymer solvent/biologically active agent non-solvent mixture wherein the amount of non-solvent achieves the biologically active agent as a microparticulate in the continuous phase and does not cause substantial precipitation of the polymer;
    b) forming droplets of the polymer/biologically active agent solution;
    c) freezing the droplets of the polymer/biologically active agent solution; and
    d) removing the continuous phase of step (a) from the polymer/biologically active agent solution, thereby forming a solid polymer/biologically active agent matrix.

16. The method of claim 15 wherein the droplets are microdroplets.

17. The method of claim 15 wherein the active agent is a peptide, an antigen or a small molecule drug.

18. The method of claim 15 wherein the active agent is an LHRH analog.

19. The method of claim 18 wherein the LHRH analog is azaline B.

20. The method of claim 15 wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

21. The method of claim 19 wherein the continuous phase comprises DMSO.

22. A method for forming a polymer-based sustained release device comprising the steps of:
    a) forming a polymer/biologically active agent solution by mixing a polymer, a continuous phase comprising one or more polymer solvents and an effective amount of the biologically active agent wherein the polymer and biologically active agent are present in relative concentrations such that the device contains about 50% by weight or more of biologically active agent;

b) forming droplets of the polymer/biologically active agent solution;

c) freezing the droplets of the polymer/biologically active agent solution; and d) removing the DMSO of step (a) thereby forming a solid polymer/active agent matrix.

23. The method of claim 21 wherein the DMSO is removed by extraction with an oil.

24. The method of claim 21 wherein the DMSO is removed by extraction with an alkane/ethanol mixture.

25. The method of claim 22 wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

26. The method of claim 22 wherein the active agent is a peptide, an antigen or a small molecule drug.

27. The method of claim 22 wherein the active agent is an LHRH analog.

28. The method of claim 27 wherein the LHRH analog is azaline B.

29. A polymer-based sustained release device produced by the steps of:

a) forming a polymer/biologically active agent solution by mixing a polymer, a continuous phase comprising one or more polymer solvents and an effective amount of the biologically active agent wherein the polymer and biologically active agent are present in relative concentrations such that the device contains about 50% by weight or more of biologically active agent;

b) forming droplets of the polymer/biologically active agent solution;

c) freezing the droplets of the polymer/biologically active agent solution; and d) removing the continuous phase of step (a) thereby forming a solid polymer/biologically active agent matrix.

30. The polymer-based sustained release device of claim 29, wherein the device is in the form of microparticles.

31. The polymer-based sustained release device of claim 29, wherein the polymer is selected from the group consisting of: poly(lactide)s, poly(glycolide)s, poly(lactide-co-glycolide)s, poly(lactic acids, poly(glycolic acid)s, poly(lactic acid-co-glycolic acid)s, blends, and copolymers thereof.

32. The polymer-based sustained release device of claim 28 wherein the active agent is a peptide, an antigen or a small molecule drug.

33. The polymer-based sustained release device of claim 28 wherein the active agent is an LHRH analog.

34. The polymer-based sustained release device of claim 32 wherein the LHRH analog is azaline B.

35. A polymer-based sustained release device produced by the steps of:

a) forming a polymer/biologically active agent solution by mixing a polymer, a continuous phase comprising a polymer solvent/polymer non-solvent mixture and an effective amount of the biologically active agent wherein the polymer and biologically active agent are present in relative concentrations such that the device contains about 50% by weight or more of biologically active agent, and the amount of polymer non-solvent achieves solubilization of the biologically active agent and does not cause substantial precipitation of the polymer;

b) forming droplets of the polymer/biologically active agent solution;

c) freezing the droplets of the polymer/biologically active agent solution; and d) removing the continuous phase of step (a) thereby forming a solid polymer/biologically active agent matrix.

36. The polymer-based sustained release device of claim 35, wherein the device is in the form of microparticles.

37. The polymer-based sustained release device of claim 35, wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

38. The polymer-based sustained release device of claim 35 wherein the active agent is a peptide, an antigen or a small molecule drug.

39. The polymer-based sustained release device of claim 35 wherein the active agent is an LHRH analog.

40. The polymer-based sustained release device of claim 35 wherein the LHRH analog is azaline B.

41. A polymer-based sustained release device produced by the steps of:

a) forming a polymer/biologically active agent solution by mixing a polymer, a continuous phase comprising a polymer solvent/biologically active agent non-solvent mixture and an effective amount of the biologically active agent wherein the polymer and biologically active agent are present in relative concentrations such that the device contains about 50% by weight or more of biologically active agent, and the amount of polymer non-solvent achieves solubilization of the biologically active agent and does not cause substantial precipitation of the polymer;

b) forming droplets of the polymer/biologically active agent solution;

c) freezing the droplets of the polymer/biologically active agent solution; and d) removing the continuous phase of step (a) thereby forming a solid polymer/biologically active agent matrix.

42. The polymer-based sustained release device of claim 41, wherein the device is in the form of microparticles.

43. The polymer-based sustained release device of claim 41, wherein the polymer is selected from the group consisting of: poly(lactide)s, poly(glycolide)s, poly(lactide-co-glycolide)s, poly(lactic acid)s, poly(glycolic acid)s, poly(lactic acid-co-glycolic acid)s, blends, and copolymers thereof.

44. The polymer-based sustained release device of claim 41 wherein the active agent is a peptide, an antigen, or a small molecule drug.

45. The polymer-based sustained release device of claim 41 wherein the active agent is an LHRH analog.

46. The polymer-based sustained release device of claim 41 wherein the LHRH analog is azaline B.

47. A polymer-based sustained release device produced by the steps of:

a) forming a polymer/biologically active agent solution by mixing a polymer, an effective amount of the biologically active agent and a continuous phase comprising a polymer solvent/biologically active agent non-solvent mixture wherein the polymer and biologically active agent are present in relative concentrations such that the device contains about 50% by weight or more of biologically active agent, and the amount of polymer non-solvent achieves the biologically active agent as a microparticulate in the continuous phase and does not cause substantial precipitation of the polymer;

b) forming droplets of the polymer/biologically active agent solution;

c) freezing the droplets of the polymer/biologically active agent solution; and d) removing the continuous phase of step (a) thereby forming a solid polymer/biologically active agent matrix.

48. The polymer-based sustained release device of claim 47, wherein the device is in the form of microparticles.

49. The polymer-based sustained release device of claim 47, wherein the polymer is selected from the group consisting of: poly(lactide)s poly(glycolide)s, poly(lactide-co-glycolide)s, poly(lactic acid)s, poly(glycolic acid)s, poly (lactic acid-co-glycolic acid)s, blends, and copolymers thereof.

50. The polymer-based sustained release device of claim 47 wherein the active agent is a peptide, an antigen or a small molecule drug.

51. The polymer-based sustained release device of claim 47 wherein the active agent is an LHRH analog.

52. The polymer-based sustained release device of claim 47 wherein the LHRH analog is azaline B.

* * * * *

UNITED STATES PATENT AND TRADEMARK OFFICE
CERTIFICATE OF CORRECTION

PATENT NO.     : 6,455,074 B1                                              Page 1 of 1
DATED          : September 24, 2002
INVENTOR(S)    : Mark A. Tracy et al.

It is certified that error appears in the above-identified patent and that said Letters Patent is hereby corrected as shown below:

<u>Column 22,</u>
Line 62, delete "claim 19", insert -- claim 22 --.

<u>Column 23,</u>
Line 56, delete "claim 28", insert -- claim 29 --.
Line 59, delete "claim 28", insert -- claim 29 --.
Line 61, delete "claim 32", insert -- claim 33 --.

Signed and Sealed this

Eleventh Day of March, 2003

JAMES E. ROGAN
*Director of the United States Patent and Trademark Office*